US011406470B2

(12) United States Patent
Jones et al.

(10) Patent No.: US 11,406,470 B2
(45) Date of Patent: Aug. 9, 2022

(54) TRAJECTORY GUIDE WITH DOUBLE X-Y SLIDING TABLES

(71) Applicant: ADVANCED NEUROMODULATION SYSTEMS, INC., Plano, TX (US)

(72) Inventors: Robert E. Jones, McKinney, TX (US); Galen L. Smith, Allen, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 824 days.

(21) Appl. No.: 16/265,674

(22) Filed: Feb. 1, 2019

(65) Prior Publication Data

US 2020/0246099 A1 Aug. 6, 2020

(51) Int. Cl.
*A61B 90/11* (2016.01)
*A61B 90/50* (2016.01)
(Continued)

(52) U.S. Cl.
CPC .............. *A61B 90/11* (2016.02); *A61B 90/50* (2016.02); *A61B 1/3135* (2013.01); *A61B 5/24* (2021.01);
(Continued)

(58) Field of Classification Search
CPC ....... A61B 90/11; A61B 90/50; A61B 1/3135; A61B 1/01; A61B 5/24; A61B 5/6868; A61B 10/04; A61B 2017/00911; A61B 2017/3407; A61B 2017/3409; A61B 2018/00446; A61B 2018/00577;
(Continued)

(56) References Cited

U.S. PATENT DOCUMENTS

| 2,948,168 A | 8/1960 | McCormick |
| 4,955,891 A | 9/1990 | Carol |

(Continued)

FOREIGN PATENT DOCUMENTS

| CN | 105232126 A | 1/2016 |
| GB | 922007 | 3/1963 |
| WO | 2019157070 A1 | 8/2019 |

OTHER PUBLICATIONS

ISA/US, Written Opinion and International Search Report, Application No. PCT/US2020/015650, dated May 25, 2020, 15 pgs.
(Continued)

*Primary Examiner* — Brooke Nicole Labranche
(74) *Attorney, Agent, or Firm* — Norton Rose Fulbright US LLP

(57) ABSTRACT

A trajectory guiding apparatus and one or more methods associated therewith for facilitating precision-guided alignment and implantation of a DBS therapy device in a patient. A base plate and base frame combination provides a platform for a dual-stage slider (DSS) assembly comprising a bottom stage slider (BSS) table and a top stage slider (TSS) table that each have suitably sized apertures or orifices therethrough for allowing the passage of and securely holding an instrumentation column (IC) assembly whose translational movement (i.e., sideways or forward and/or backward directions along a translational plane) and pivotal/rotational movement (i.e., around a perpendicular axis orthogonal to the translational plane and extending through a pivot or fulcrum) are independently controlled by respective slide actuators in order to properly align the IC assembly to a desired trajectory.

16 Claims, 9 Drawing Sheets

(51) Int. Cl.
    *A61B 17/34*     (2006.01)
    *A61B 1/313*     (2006.01)
    *A61B 10/04*     (2006.01)
    *A61B 18/00*     (2006.01)
    *A61M 25/01*     (2006.01)
    *A61B 90/10*     (2016.01)
    *A61B 17/00*     (2006.01)
    *A61N 1/05*     (2006.01)
    *A61B 5/24*     (2021.01)

(52) U.S. Cl.
    CPC ..... *A61B 10/04* (2013.01); *A61B 2017/00911* (2013.01); *A61B 2017/3407* (2013.01); *A61B 2017/3409* (2013.01); *A61B 2018/00446* (2013.01); *A61B 2018/00577* (2013.01); *A61B 2090/103* (2016.02); *A61B 2217/005* (2013.01); *A61B 2217/007* (2013.01); *A61M 25/01* (2013.01); *A61N 1/0534* (2013.01)

(58) Field of Classification Search
    CPC ...... A61B 2090/103; A61B 2090/0807; A61B 2217/005; A61B 2217/007; A61B 34/20; A61B 2560/063; A61M 25/01; A61N 1/0534; A61N 1/372
    See application file for complete search history.

(56) References Cited

U.S. PATENT DOCUMENTS

| | | | |
|---|---|---|---|
| 5,094,243 | A | 3/1992 | Puy et al. |
| 5,154,723 | A | 10/1992 | Kubota et al. |
| 6,491,699 | B1 | 12/2002 | Henderson et al. |
| 7,736,371 | B2 | 6/2010 | Schoepp |
| 7,949,410 | B2 | 5/2011 | Rodriguez |
| 8,463,387 | B2 | 6/2013 | De Ridder |
| 8,747,418 | B2 | 6/2014 | Qureshi et al. |
| 9,192,446 | B2 | 11/2015 | Piferi et al. |
| 9,232,977 | B1 | 1/2016 | Rehman et al. |
| 9,370,653 | B2 | 6/2016 | Sefkow et al. |
| 10,456,201 | B1 | 10/2019 | Solar et al. |
| 2001/0053879 | A1 | 12/2001 | Mills et al. |
| 2006/0122627 | A1 | 6/2006 | Miller et al. |
| 2008/0306375 | A1 | 12/2008 | Sayler et al. |
| 2009/0131783 | A1 | 5/2009 | Jenkins et al. |
| 2010/0042111 | A1 | 2/2010 | Qureshi et al. |
| 2011/0190787 | A1 | 8/2011 | Sahni |
| 2011/0237881 | A1 | 9/2011 | Kunz |
| 2014/0024927 | A1 | 1/2014 | Piferi |
| 2017/0311978 | A1 | 11/2017 | Chieng |
| 2018/0008821 | A1 | 1/2018 | Gonzalez et al. |
| 2020/0246099 | A1 | 8/2020 | Jones et al. |
| 2020/0246100 | A1 | 8/2020 | Jones et al. |
| 2020/0246101 | A1 | 8/2020 | Jones et al. |
| 2020/0390465 | A1 | 12/2020 | Lopez |

OTHER PUBLICATIONS

ISA/US, Written Opinion and International Search Report, Application No. PCT/US2020/015702, dated May 25, 2020, 13 pgs.
ISA/US, Written Opinion and International Search Report, Application No. PCT/US2020/015849, dated May 25, 2020, 16 pgs.
ISA/US, Written Opinion and International Search Report, Application No. PCT/US2020/015650, dated May 21, 2020, 15 pgs.
ISA/US, Written Opinion and International Search Report, Application No. PCT/US2020/015702, dated Apr. 1, 2020, 13 pgs.
ISA/US, Written Opinion and International Search Report, Application No. PCT/US2020/015849, dated Jun. 9, 2020, 16 pgs.

TRAJECTORY GUIDE WITH DOUBLE X-Y SLIDING TABLES

CROSS-REFERENCE TO RELATED APPLICATION(S)

This application discloses subject matter that is related to the subject matter of the following U.S. patent application(s): (i) "TRAJECTORY GUIDE WITH DUAL GIMBAL DRIVE ARRANGEMENT", application Ser. No. 16/265,704, filed Feb. 1, 2019, in the name(s) of Robert Jones and Galen L. Smith; and (ii) "TRAJECTORY GUIDE WITH DUAL ARC ARRANGEMENT", application Ser. No. 16/265,737, filed Feb. 1, 2019, in the name(s) of Galen L. Smith and Robert Jones; each of which is hereby incorporated by reference in its entirety.

TECHNICAL FIELD

The present disclosure generally relates to surgical platforms used in medical device placement. More particularly, and not by way of any limitation, the present disclosure is directed to a trajectory guide and associated method for providing trajectory alignment and implantation of a therapy device in a patient.

BACKGROUND

The use electrical stimulation for treating neurological disease, including such disorders as movement disorders including Parkinson's disease, essential tremor, dystonia, chronic pain, and the like has been widely discussed in the literature. In many instances, the preferred objective is to modulate neuronal activity in certain known target areas of the central nervous system of a patient. Electrical stimulation permits such modulation of the target neural structures, e.g., various regions in the patient's brain, and, equally importantly, does not require the destruction of nervous tissue. Efforts have also been underway to treat psychiatric disorders with peripheral/cranial nerve stimulation such as, e.g., depression, compulsive eating disorders, etc.

Deep brain stimulation (DBS) refers to the delivery of electrical pulses into one or several specific sites within the brain of a patient to treat various disorders. For example, DBS has been proposed as a clinical technique for treatment of chronic pain, essential tremor, Parkinson's disease (PD), dystonia, epilepsy, depression, obsessive-compulsive disorder, and other disorders.

Stereotactic neurosurgery is a field of neurosurgery in which an implantable medical device is advanced through a burr hole in the cranium of a patient to a target region of interest by means of a mechanical device attached to the skull with aiming based on pre-operative and/or intraoperative imaging. For the past decade or so, the field has been advancing from using large, classical metal frames (e.g., "center-of-arc" systems), which typically encompass the entire head of a patient, to the attachment of small platforms placed only over an entry site (commonly referred to as "frameless" or "microframe" technologies).

Whereas advances in stereotactic surgical instrumentation and devices continue to grow apace, several lacunae remain, thereby requiring further innovation as will be set forth hereinbelow.

SUMMARY

Embodiments set forth herein are directed to a trajectory guiding apparatus and one or more methods associated therewith for facilitating precision-guided alignment and implantation of a therapy device in a patient while providing reduced patient discomfort, ease of surgical access, and other benefits that will become apparent from the description herein.

In one aspect, an example trajectory guiding apparatus according to an embodiment of the present patent disclosure comprises, inter alia, a base plate comprising a frame portion with a plurality of laterally extending support members, the frame portion having a first aperture sized to surround a burr hole opening in a patient's cranium, the frame portion configured for fastening the base plate to the cranium; a base frame comprising a plurality of legs corresponding to the plurality of laterally extending support members of the base plate, each leg having a top terminus and a bottom terminus, wherein the plurality of legs are securely coupled at respective bottom termini to the corresponding laterally extending support members; and a first platform securely coupled to the plurality of legs at respective top termini, the first platform having a second aperture with at least a same size as the first aperture of the frame portion; and a dual-stage slider (DSS) assembly comprising a bottom stage slider (BSS) table and a top stage slider (TSS) table, the BSS table slidably engaged to the first platform and the TSS table coupled to the BSS table via a second platform disposed between the BSS table and the TSS table, the second platform having a third aperture, wherein the BSS table is provided with a first funnel extending toward the burr hole and configured to contain a bottom spherical bearing having a first diameter and the TSS table is provided with a second funnel configured to contain a top spherical bearing having a second diameter, the bottom and top spherical bearings each having a respective axial bore therethrough, the respective axial bores axially aligned and sized to accommodate an instrumentation column (IC) having an columnar passage therethrough and coupled to a drive assembly for advancing a distal end of an implantable elongate medical device through the columnar passage of the instrumentation column.

In one example embodiment, the BSS and TSS tables are independently actuatable, wherein the BSS table is actuatable to move the instrumentation column on a translational motion plane (e.g., an X-Y plane) substantially parallel relative to a burr hole plane that is co-planar with the burr hole and the TSS table is actuatable to pivotally rotate the instrumentation column, with the bottom spherical bearing operating as a fulcrum, to change a trajectory angle of the instrumentation column relative to a perpendicular axis (e.g., the Z-axis) orthogonal to the burr hole plane.

In one example embodiment, the BSS table comprises a bottom lower plate slidably engaged with a grooved surface of the first platform; and a bottom upper plate slidably engaged with the bottom lower plate and rigidly coupled to the second platform, wherein the bottom lower plate is operative to slide along a first axis and the bottom upper plate is operative to slide along a second axis, the first and second axes orthogonal to each other and disposed along the translational motion plane.

In one example embodiment, the TSS table comprises a top lower plate slidably engaged with a grooved surface of the second platform; and a top upper plate slidably engaged with the top lower plate, wherein the top lower plate is operative to slide along the first axis and the top upper plate is operative to slide along the second axis. A translational movement of at least one of the top lower plate and the top upper plate of the TSS table is converted or otherwise transferred into a pivotal/rotational movement of the instrumentation column around the perpendicular axis by a joint action of the bottom and top spherical bearings.

In another aspect, an example method according to an embodiment of the present patent disclosure for implanting an elongate medical device into a patient's brain comprises, inter alia, obtaining trajectory path information regarding at least one of a path entry point, a target location, a trajectory path and an entry angle with respect to implanting the elongate medical device through the patient's cranium, the elongate medical device configured to provide a particular therapy; creating a burr hole in the cranium around the path entry point; attaching a trajectory guiding apparatus including an instrumentation column (IC) assembly that contains the elongate medical device, the trajectory guiding apparatus having a base plate configured to be secured to the cranium and surround the burr hole in a close proximity; adjusting a translational movement by actuating a bottom stage slider (BSS) table of the trajectory guiding apparatus to align the IC assembly to the path entry point in the burr hole; adjusting a rotational movement by actuating a top stage slider (TSS) table of the trajectory guiding apparatus to align an axial angle of the IC assembly with the entry angle; and advancing the elongate medical device using a drive assembly associated with the IC assembly until the target location is reached. In one variation, an embodiment of the method may further comprise continuing to guide the elongate medical device along the trajectory path as the elongate medical device is advanced in the patient's brain; and if a path deviation is determined, obtained or otherwise indicated, applying at least one of a translational adjustment and a rotational adjustment by actuating at least one of the BSS table and the TSS table to realign the elongate medical device with the trajectory path. In one arrangement, an embodiment of the elongate medical device may comprise at least one of a DBS lead comprising a plurality of electrodes at a distal end, a biopsy instrumentation device, a catheter insertion device, an injection and aspiration device, a neurological endoscopy device, a microelectrode recording (MER) device, a macro stimulation device, a cannula device, a neurological ablation device, and a brain lesioning device, and the like.

Additional/alternative features and variations of the embodiments will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

DETAILED DESCRIPTION

Figure 1:
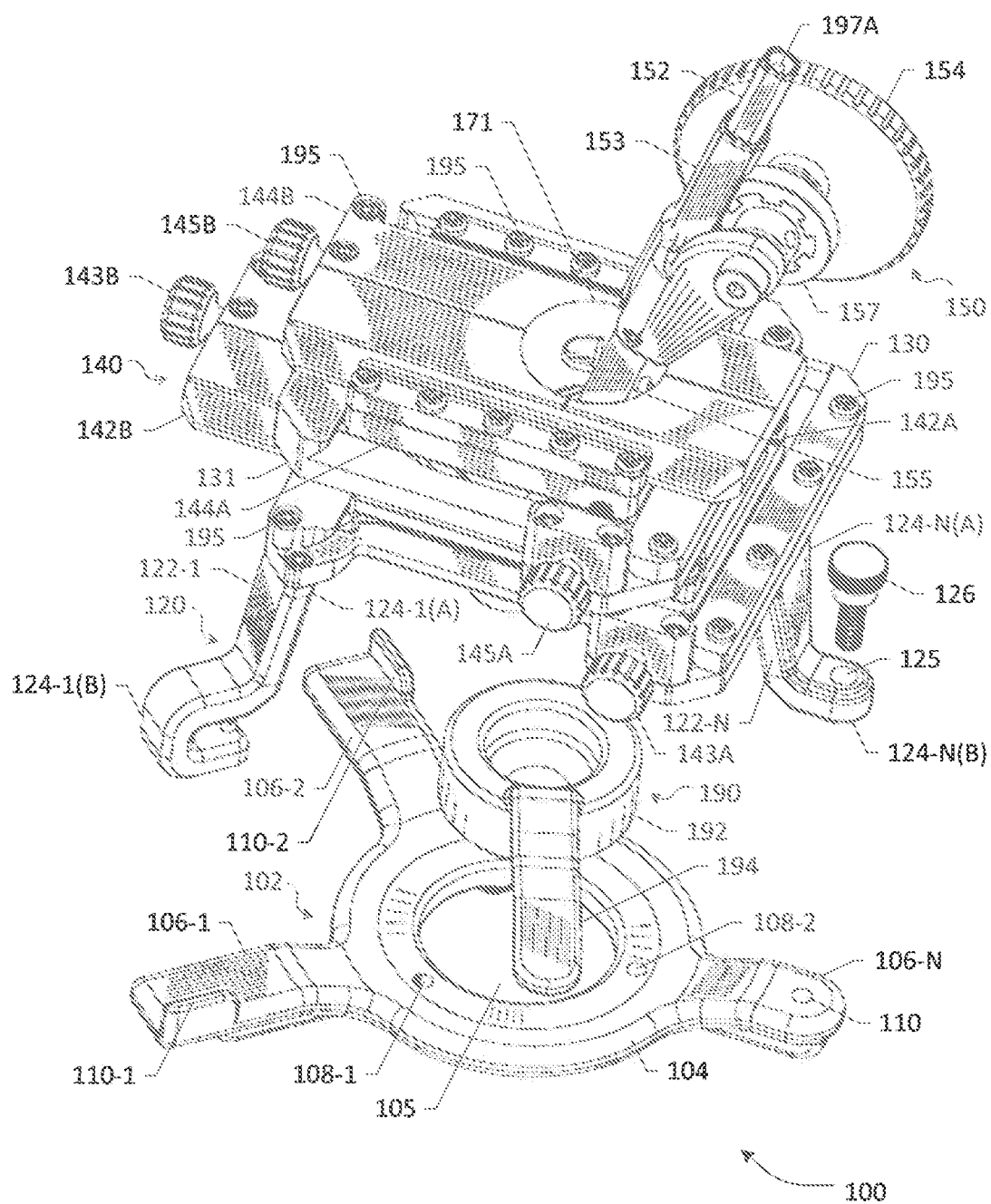
FIG. 1 depicts a 3-dimensional (3D) partially disassembled view of an example trajectory guide apparatus including a dual-stage slider assembly for effectuating independent translational and rotational movement of an instrumentation column according to an embodiment of the present patent application.

In the description herein for embodiments of the present disclosure, numerous specific details are provided, such as examples of mechanical elements, devices, components and/or methods, etc., to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an element, component or module may be configured to perform a function if the element may be constructed for performing or otherwise structurally arranged to perform that function.

Further, while reference is made to the accompanying drawing Figures that form a part hereof with respect to illustrative embodiments, it is to be understood that other embodiments, which may not be described and/or illustrated herein, are certainly contemplated. To the extent any headings, sub-titles, captions, banners, etc. are provided in the present disclosure, it should be understood that they are provided only for the convenience of the reader and not be used to limit the meaning of any text that follows the heading, sub-title, banner or caption unless so specified. Moreover, all numbers expressing quantities, and all terms expressing direction/orientation (e.g., vertical, horizontal, parallel, perpendicular, etc.) in the specification and claims are to be understood as being modifiable in all instances by the terms "about," "approximately," or terms of similar import, which may represent commonly known allowances or deviations from the quantities and directions being described unless otherwise indicated.

Referring now to the drawings wherein like or similar elements are designated with identical reference numerals throughout the several views, and wherein the various elements depicted are not necessarily drawn to scale, and referring to FIG. 1 in particular, depicted therein is a 3-dimensional (3D) partially disassembled view of an example trajectory guide apparatus 100 including a dual-stage slider assembly 140 for effectuating independent translational and rotational movement of a tubular instrumentation column (IC) or assembly 150 according to an embodiment of the present patent application. A base plate 102 comprising a frame portion 104 having a plurality of laterally extending support members 106-1 to 106-N is provided as a foundation configured for securely fastening the trajectory guide apparatus 100 to a patient's cranium, wherein the frame portion 104 is provided with a first aperture 105 roughly sized to surround a burr hole opening in the patient's cranium. In one arrangement, the burr hole may have been created based on stereotactic information comprising, e.g., predetermined target location in the patient's brain, entry point on the skull, entry angle, trajectory, etc., using any known image scanning and acquisition technology in conjunction with a suitable stereotactic apparatus configuration. In one arrangement, the frame portion 104 of the base plate 102 preferably comprises an annular structure having a circular orifice forming the first aperture 105, the circular orifice optimally sized to surround the burr hole in a close proximity. Further, in one arrangement, the frame portion 104 may be provided with a minimum number of holes (e.g., 2, 3 or more) for securely fastening the base plate 102 to the cranium with surgical screws, which may be sized and positioned in the frame portion 104 such that a firm attachment to the patient's skull can be achieved that can withstand various movements, e.g., torquing, bumping, or other potentially dislodging and/or disorienting forces that may be encountered while the patient is moved around within the surgical facility, while causing only a minimal amount discomfort to the patient during the procedure. Skilled artisans will recognize that the frame portion 104 may also be comprised of different shapes (e.g., oval, obround, elliptical, square, hexagonal, octagonal, etc.) having suitably shaped apertures and provided with a varying minimum number of fasteners in other arrangements for purposes of an embodiment of the present patent disclosure A base frame 120 comprising a plurality of legs 122-1 to 122-N corresponding to the plurality of laterally extending support members 106-1 to 106-N of the base plate 102 may be removably attached to the base plate 102, wherein the base frame 120 is operative as a load-supporting deck structure for the dual-stage slider assembly 140 and the IC assembly 150 comprising a tubular shaft 152 associated with a drive assembly 157. In general, structural components disposed above the base plate 102 and attached thereto (e.g., base portion 120, dual-stage slider assembly 140 and IC assembly 150 with associated drive assembly 157) may be considered as a "tower portion" or "mini-derrick" of the trajectory guiding apparatus 100. Each leg may be provided with a top terminus and a bottom terminus such that the plurality of legs 122-1 to 122-N are securely coupled at respective bottom termini 124-1(B) to 124-N(B) to the corresponding laterally extending support members 106-1 to 106-N. A first platform 130 is securely coupled to the plurality of legs 122-1 to 122-N at respective top termini 124-1(A) to 124-N(A), wherein the first platform 130 is provided with a second aperture (not shown in this FIG.) with at least a same size as the first aperture 105 of the frame portion 104. In one arrangement, at least one of the plurality of legs, e.g., leg 122-N, may be coupled in a "semi-permanent" manner to a corresponding laterally extending support member 106-N of the base plate 102 with a screw, bolt, or other fastener 126 that may be driven through a threaded or unthreaded hole 125 of the bottom terminus 124-N(B) of leg 122-N and a corresponding threaded or unthreaded hole 110 of the lateral support member 106-N. Remaining legs may be removably attached to corresponding laterally extending support members of the base plate 102 in a sliding or snapping fit arrangement (e.g., snap fit, friction fit, interference fit, press fit, etc.) to facilitate ease of disassembly of the base frame 120 from the base plate 102. In such an arrangement, the bottom termini of the legs and/or the distal ends of the corresponding lateral support members may be suitably modified to effectuate the fitting arrangement. By way of example, the bottom terminus 124-1(B) of leg 122-1 is modified to have a shape, e.g., a hooked foot, that can be slidably snapped into a distal end of the corresponding lateral supporting member 106-1 that is provided with a rib, rim, collar or flange and the like, shown as a vertical tab 110-1, to arrest and lock the hooked foot after snapping/sliding into place.

In an embodiment where the base plate 102 is provided with three laterally extending support members (e.g., radially and laterally extending at a 120° angle with respect to each other from the frame portion 104), the base frame 120 comprises three corresponding legs 122-1 to 122-3 that may also be spaced apart correspondingly, thereby facilitating a fairly unhindered access to the burr hole region of the patient's cranium while still providing structural strength to the trajectory guide apparatus 100. Skilled artisans will therefore recognize that the base plate and base frame arrangement 102/120 disclosed herein advantageously not only provides geometric stability of the apparatus 100 but also maximizes access to the burr hole to allow intraoperative (i.e., during a procedure) surgical manipulation, as access to the burr hole is critically important for the purposes of, inter alia, attending to any bleeding from the bone cavity, dura, and the surface of the cortex during the procedure, (re)positioning of any implantable medical instrumentation, alignment tools, etc.

In an example embodiment, dual-stage slider (DSS) assembly 140 comprises a first or bottom stage slider (BSS) table and a second or top stage slider (TSS) table that each have suitably sized apertures or orifices therethrough for allowing the passage of and securely holding the IC assembly 150 whose translational movement(s) (i.e., sideways or forward and/or backward directions and/or in any cardinal direction along a translational plane) and rotational movement(s) (i.e., around a perpendicular axis orthogonal to the translational plane and extending through a pivot or fulcrum) are independently controlled by respective slide actuators in order to properly align the IC assembly 150 holding an elongate medical device (not shown in this FIG.) with respect to an implant trajectory path and entry point with respect to the burr hole. Preferably the BSS table comprises an X-Y slider table (e.g., a first X-Y slider table) including a bottom lower plate 142A that is slidably engaged or otherwise articulated with a grooved surface of the first platform 130 and actuated by a screw drive 143A and a bottom upper plate 142B slidably engaged or otherwise articulated with the bottom lower plate 142A and coupled to a second platform 131 (also having an aperture or orifice, not shown in this FIG.), the bottom upper plate 142B being actuatable by a corresponding screw drive 143B. Likewise, the TSS table also comprises an X-Y slider table (i.e., a second X-Y slider table) including a top lower plate 144A slidably engaged or otherwise engaged with a grooved surface the second platform 131 having an aperture, the top lower plate 144A being actuatable by a screw drive 145A. A top upper plate 144B is slidably articulated or otherwise engaged with the top lower plate 144A, wherein the top upper plate 144B is actuated by a corresponding screw drive 145B. As will be described further below, whereas the translational movement of the BSS table 142A/142B is operative to move the IC assembly 150 along a translational motion plane parallel to the burr hole plane, the translational movement of the TSS table 144A/144B is converted or otherwise transferred to a pivotal rotational movement of the IC assembly 150 around the perpendicular axis (i.e., the Z-axis in a 3D Cartesian coordinate system relative to the X-Y sliding tables) to control the trajectory angle of an implantable medical device housed and advanced through the IC assembly 150.

For purposes of the present patent application, remaining descriptive portions of the trajectory guiding apparatus 100 will be set forth below by taking reference to FIGS. 2-6 in conjunction with FIG. 1, wherein the trajectory guiding apparatus 100 is depicted in different views, with the foregoing description being applicable, mutatis mutandis, as necessary.

Figure 2:
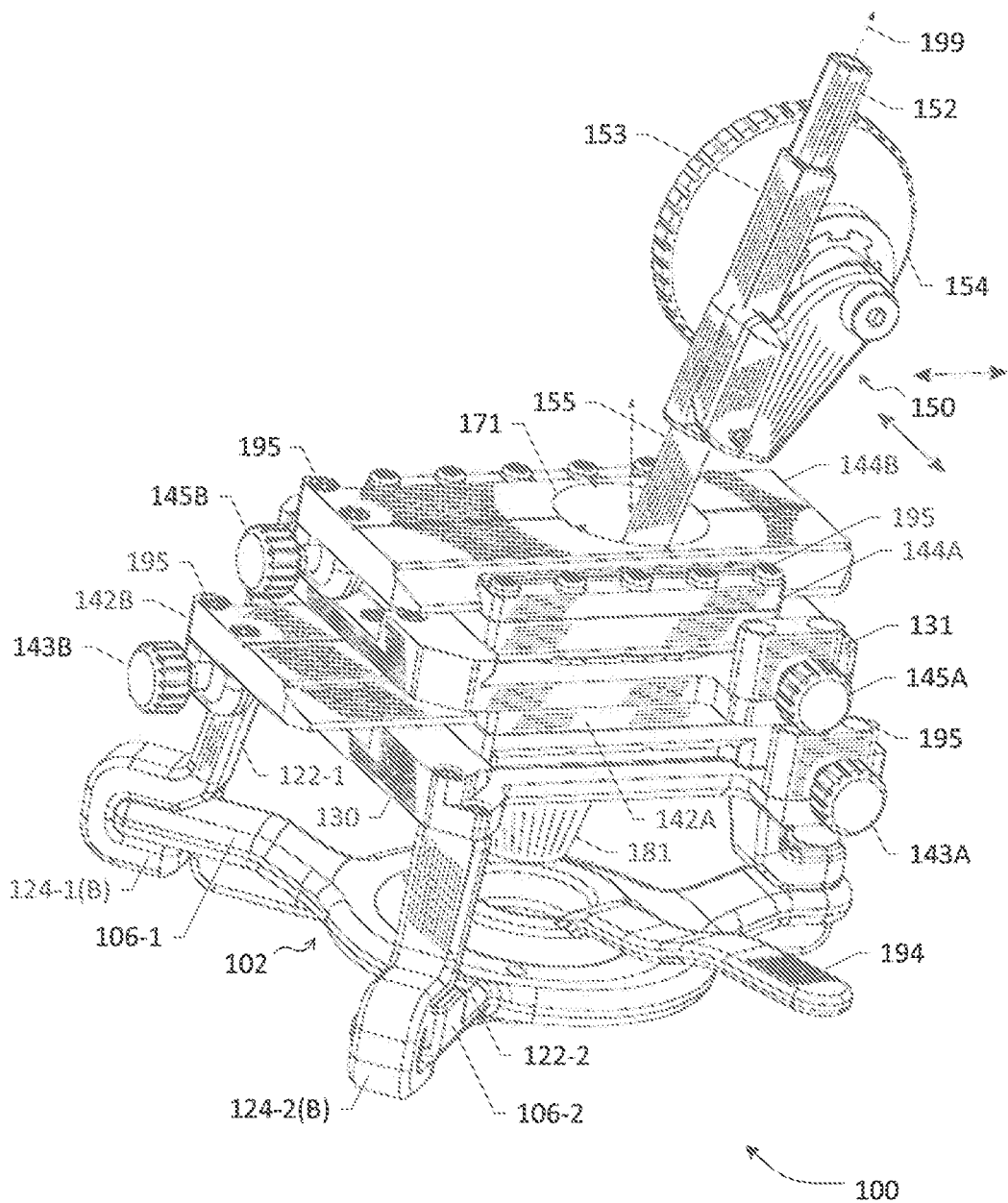
FIG. 2 depicts a 3D isometric view of the example trajectory guide apparatus of FIG. 1.
Figure 3:
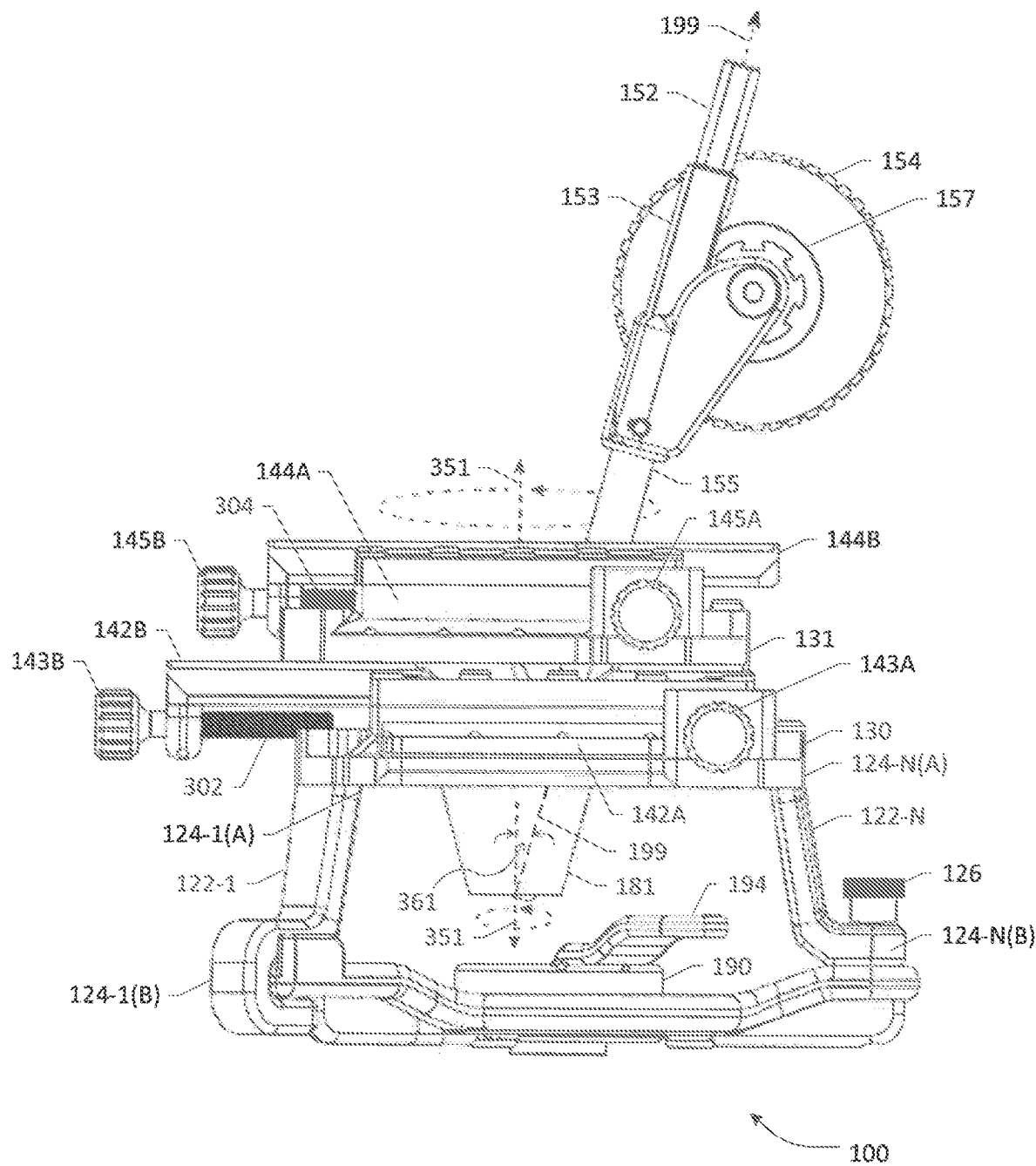
FIG. 3 depicts a side view of the example trajectory guide apparatus of FIG. 1.
Figure 4:
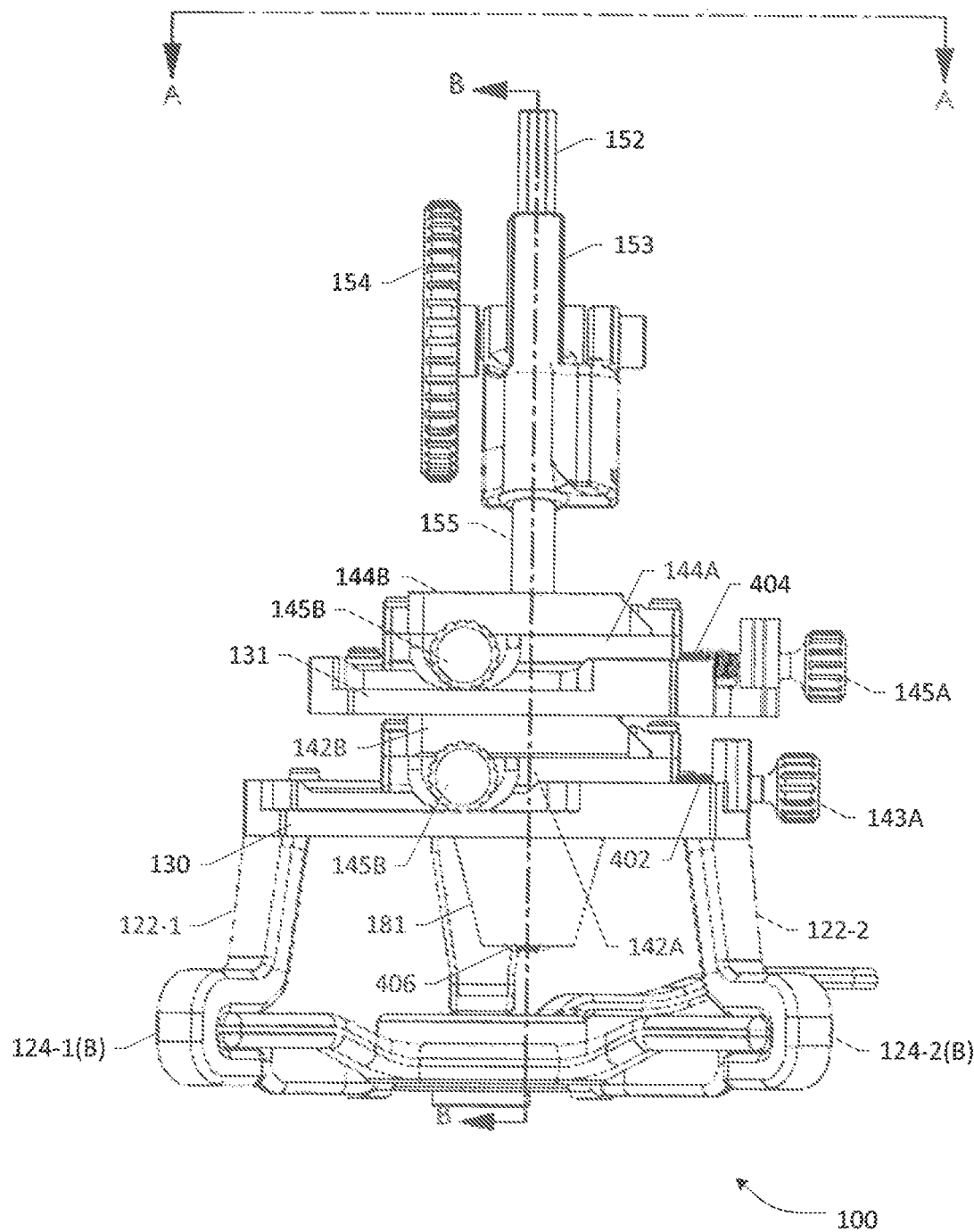
FIG. 4 depicts a front view of the example trajectory guide apparatus of FIG. 1.
Figure 5:
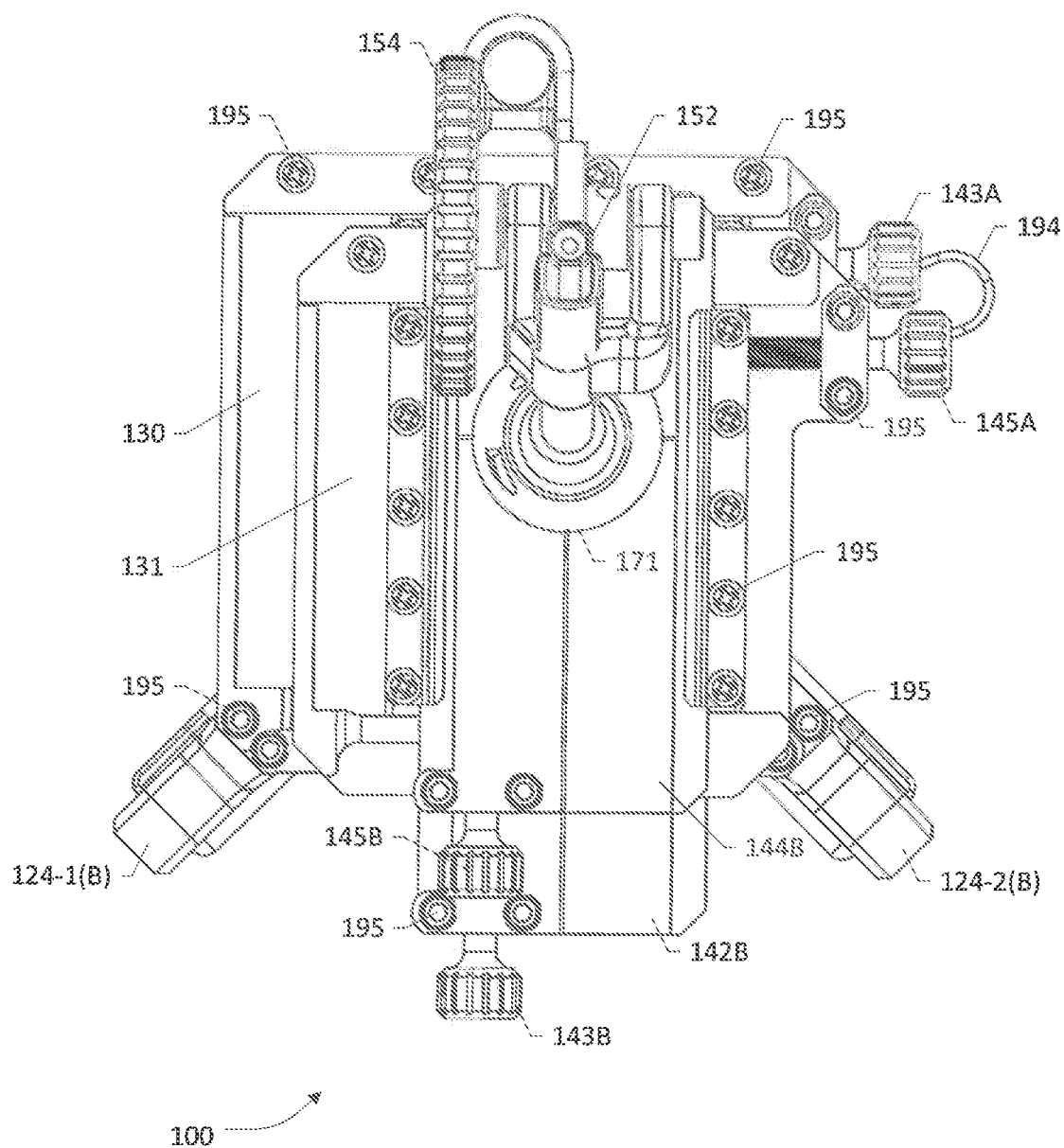
FIG. 5 depicts a top view of the example trajectory guide apparatus of FIG. 1 viewed from the A-A plane shown in FIG. 4.
Figure 6:
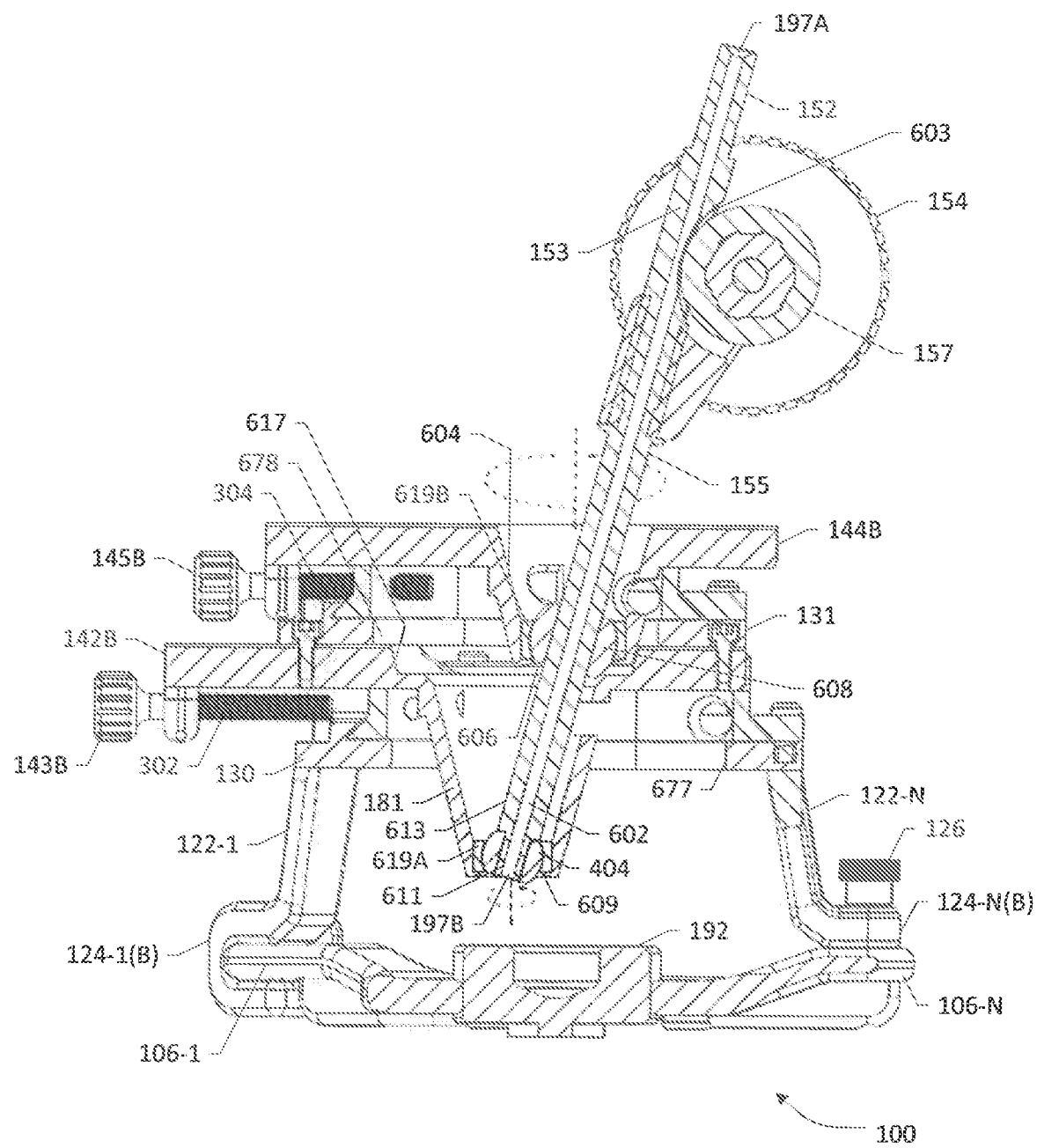
FIG. 6 depicts a partial cutaway or cross-sectional view of the example trajectory guide apparatus of FIG. 1 along the B-B plane shown in FIG. 4.

FIG. 2 depicts a 3D isometric view of the example trajectory guide apparatus 100 of FIG. 1 as assembled. FIG. 3 depicts a side view of the example trajectory guide apparatus 100. FIG. 4 depicts a front view of the example trajectory guide apparatus 100. FIG. 5 depicts a top view of the example trajectory guide apparatus 100 viewed from the A-A plane shown in FIG. 4. FIG. 6 depicts a partial cutaway or cross-sectional view of the example trajectory guide apparatus 100 along the B-B plane shown in FIG. 4. In one representative arrangement, exemplified by the cutaway view shown in FIG. 6, the BSS table 142A/B is provided with a first or bottom spherical bearing 406 having a first diameter and the TSS table 144A/144B is provided with a second or top spherical bearing 608 having a second diameter larger than the first diameter, wherein the bottom and top spherical bearings 406, 608 each have a respective axial bore therethrough and are operative to rotate independent from each other when not engaged by the IC assembly 150. The respective axial bores may be axially aligned and sized to accommodate a first shaft portion 155 of the IC assembly 150. Preferably, the axial bore of the bottom spherical bearing 406 is narrower than the axial bore of the top spherical bearing 608 such that a distal end 613 of the first shaft portion 155 of the IC assembly 150 is thinned or otherwise reduced in size to a narrow tip 611 that can be accommodated as a pivot in the axial bore of the bottom spherical bearing 406 such that the bottom spherical bearing 406 can operate as a fulcrum or ball joint for the IC assembly 150. To accommodate the bottom spherical bearing 406, a first or bottom slider aperture 617 is defined through the bottom upper plate 142B and the bottom lower plate 142A, wherein the first slider aperture 617 may be tapered or angled or stepped from a wider orifice at the bottom upper plate 142B, which tapers and extends through the bottom lower plate 142A into a funnel 181 (e.g., a first funnel, stemless or short-stem funnel or similar structure) coupled to the bottom lower plate 142A and opens toward the burr hole. It should be appreciated that an aperture 677 provided in the first platform 130 (i.e., the second aperture) allows the passage of the funnel 181 therethrough. The funnel 181 tapers or steps down to a narrow orifice 609 proximately facing but spaced away from the burr hole, wherein the orifice 609 is sized to contain a first or bottom ring liner 619A, e.g., an O-ring sealing/cushioning washer, operative to securely hold the bottom spherical bearing 406 while allowing rotational movement. Because of the aperture 677 in the first platform 130, which is wider than the aperture 105 of the frame portion 104 as noted previously, the funnel 181 may be moved around laterally/translationally as the screw drives 143A/143B are actuated. Being disposed in an X-Y slider arrangement, the bottom lower plate 142A is operative to slide along a first axis (e.g., X-axis, depending on how a Cartesian coordinate system is referenced with respect to the trajectory guide apparatus 100) whereas the bottom upper plate 142B is operative to slide along a second axis (e.g., Y-axis), wherein the first and second axes are orthogonal to each other and lie on or otherwise define the translational movement plane that is parallel to the burr hole plane. It will be realized that if the burr hole is placed on top of the cranium such that the trajectory guide apparatus 100 is vertically affixed to the skull and aligned to the sagittal plane of the patient, the translational motion plane will be horizontal and perpendicular with respect thereto. On the other hand, if the burr hole is placed on a side of the patient's cranium, the vertical axis of trajectory guide apparatus 100 will be angularly displaced from the sagittal or coronal plane of the cranium. Accordingly, the translational motion plane of the slider assembly 142A/142B will also be at an angle to the sagittal or coronal plane of the patient while being parallel to the burr hole plane.

To accommodate the top spherical bearing 608, a second or top slider aperture 171 is defined through the top upper plate 144B and the top lower plate 144A, wherein the second slider aperture 171 may be tapered or angled or stepped from a wider orifice at the top upper plate 144B extending through the top lower plate 144A as a stemless funnel 604 (e.g., a second funnel or similar structure) having an angled surface, wherein the aperture 171 tapers from a wider orifice at the top upper plate 144B to a narrow orifice 606 at the top lower plate 144A such that it is sized to contain a second or top ring liner 619B, e.g., an O-ring sealing/cushioning washer, operative to securely hold the top spherical bearing 608 while allowing rotational movement. As noted previously, the second platform 131 to which the top lower plate 144A of the TSS assembly is affixed is provided with aperture 678 (i.e., a third aperture) that is dimensioned such that while the TSS table is moved laterally or translationally (as the BSS table is laterally or translationally moved), the narrow orifice 606 of funnel 604 stays within the area of the first slider table aperture 617.

When the IC assembly 150 is inserted into or otherwise engaged with the bottom and top spherical bearings 406, 608, a linear movement of the top lower and upper plates 144A/144B caused by actuating the corresponding screw drives 145A/145B is converted or transferred into a rotational movement by the top spherical bearing 608, which causes a pivotal motion of the IC assembly 150 with respect to the perpendicular axis 351 (e.g., similar to a ball-and-socket or universal joint that allows multidirectional movement and rotation) such that a longitudinal axis 199 of the IC assembly 150 moves around or toward or away from the perpendicular axis 351 in a 3D space, thereby changing an angle ($\phi$) 361 therebetween along any vertical plane perpendicular to the translational motion plane.

In one arrangement, the IC assembly 150 includes a columnar passage 602 having a proximate opening 197A and a distal opening 197B, wherein the columnar passage 602 may be sized to accommodate a suitable elongate medical device specific to the therapy application. By way of illustration, example medical devices may comprise, without limitation, any type or variety of DBS leads, each comprising a plurality of electrodes at a distal end in a host of configurations (e.g., percutaneous leads, paddle leads, etc.) having ring electrodes, segmented electrodes, pad electrodes, and the like), biopsy instrumentation devices, catheter insertion devices, injection and aspiration devices, neurological endoscopy devices, microelectrode recording (MER) devices, macro stimulation devices, cannulas, stylets having a flexible wire (e.g., a guide wire) or similar delivery structures, neurological ablation devices, and brain lesioning devices, and the like, generally referred to herein as "instrumentation" or "implantable medical devices." Whereas at least a portion of the IC assembly 150 or its tubular shaft 152 may form a portion that is shaped and dimensioned to allow insertion into and engagement with the bottom and top spherical ball joints 406, 608 (e.g., first shaft portion 155), a second shaft portion 153 thereof may be shaped and dimensioned to facilitate the formation of a vertical opening 603 to the internal columnar passage 602 in order to allow a tension member 157 of a drive assembly 154 to frictionally hold the elongate medical device within the columnar passage 602. In one arrangement, the drive assembly 154 may be manually operable to introduce and advance the elongate medical device toward and through the burr hole along a trajectory. In another arrangement, a motorized drive assembly may be provided to automate the advancement of the elongate medical device (e.g., (tele)robotically, based on a suitable medical guided positioning or navigation system in conjunction with bio-imaging/scanning systems).

As noted previously, the bottom lower and upper plates 142A/142B as well as the top lower and upper plates 144A/144B are each actuated by a corresponding screw drive 143A/143B, 145A/145B. Similar to the IC drive assembly 154, the screw drives 143A/143B, 145A/145B may be manually operable by a medical professional to adjust the lateral positioning and/or the angular orientation of the IC assembly 150 during a procedure, i.e., intraoperatively, in order to guide and/or align and the implant trajectory of an elongate medical device. In another arrangement, a motorized drive assembly may be provided to automate the translational and/or rotational movement of the elongate medical device (e.g., using (tele)robotics and guided positioning/navigation systems as noted previously). It will be apparent to skilled artisans that the various screw drives as well as the IC drive assembly may be configured to provide both micro adjustments (i.e., adjustments with fine granularity) and macro adjustments (i.e., adjustments with coarse granularity) with respect to any of the axial movement, translational movement or pivotal/rotational movement of the elongate medical device. In one arrangement, any combination of the bottom lower plate 142A, the bottom upper plate 142B, the top lower plate 144A and the top upper plate 144B may be provided with corresponding measurement gauges, scales (e.g., main and/or vernier scales), etc., for providing a visual indication and/or measurement of at least one of a translational movement and a rotational movement as the screw drives are manipulated to guide the positioning of the IC assembly 150. Likewise, a portion of either shaft portions 153, 155 of the IC assembly 150 may also be provided with a similar corresponding measurement gauge or scale to provide an indication or measurement of the axial or longitudinal movement of the elongate medical device, which can facilitate a determination of how far the distal end of the elongate medical device has gone in the patient's brain (i.e., a depth measurement). Where screw drives or gear-based drives are employed, the amount of movement, distance or displacement may be varied based on the gear ratios, thread size, etc., provided with the respective mechanical elements, e.g., shafts 302, 304, 402, 404, drive assembly 154, etc., to achieve finer or coarser granular control in the positioning of the IC assembly 150.

In a further example embodiment, a removable burr hole alignment tool 190 may also be optionally employed in association with the base plate 102 to facilitate alignment between a burr hole in the patient's cranium and the positioning of an apparatus such as the trajectory guide apparatus 100. In such an arrangement, the removable burr hole alignment tool 190 may be provided as an annular ring 192 having a handle 194 extending therefrom, wherein the annular ring 192 may be dimensioned and contoured to achieve a snug fit between the burr hole and the aperture 105 of the frame portion 104 when the alignment tool 190 is placed in the burr hole.

Skilled artisans will further recognize that the various structural components and elements of the trajectory guide apparatus 100 set forth herein may be formed, manufactured, assembled, or otherwise fabricated using any known or heretofore unknown technologies (e.g., injection molding, casting, 3D-printing, etc.) involving suitable materials, preferably comprising biocompatible and magnetic resonance imaging (MRI)-compatible materials, such that the trajectory guide apparatus 100 may be deployed in a broad range of therapy applications and settings including where MRI, X-ray, or other radiation-based imaging technologies and systems are used. Accordingly, example non-metallic or non-magnetic materials may include but not limited to thermoplastic polymers, synthetic or semi-synthetic plastics, thermosetting polymers, elastomers, crystalline or non-crystalline amorphous solids, and the like. Components requiring a rigid or firm coupling with other components of the trajectory guide apparatus 100 may be provided with a variety of fastening means 195, 126, such as, e.g., screws, bolts, rivets, binder posts, etc., which may also be formed or fabricated from bio/MRI-compatible materials. Further, whereas various structural elements may be rigidly or semi-rigidly coupled together to form further components or assemblies, it will be understood such components or assemblies may be formed in a unitary construction process such that they form a single structure, preferably of bio/MRI-compatible materials having suitable structural properties. Likewise, various screw drive mechanisms and/or IC drive assembly mechanisms may also be fabricated from similar compatible materials.

Figure 7A:
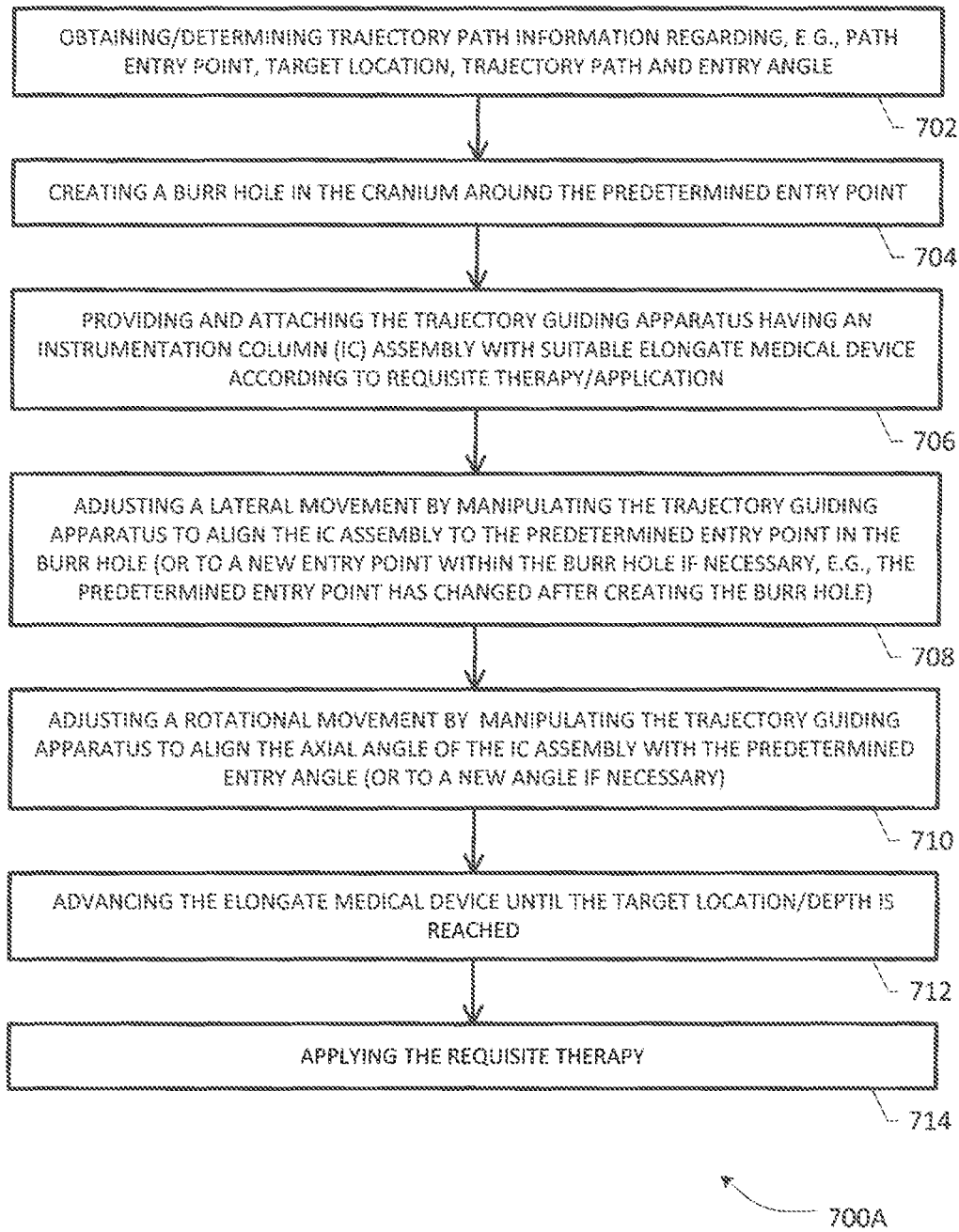
FIGS. 7A and 7B depict flowcharts of various steps, blocks, acts and/or functions that may be combined in one or more (re)arrangements for purposes of practicing a method according to an example embodiment of the present disclosure.
Figure 7B:
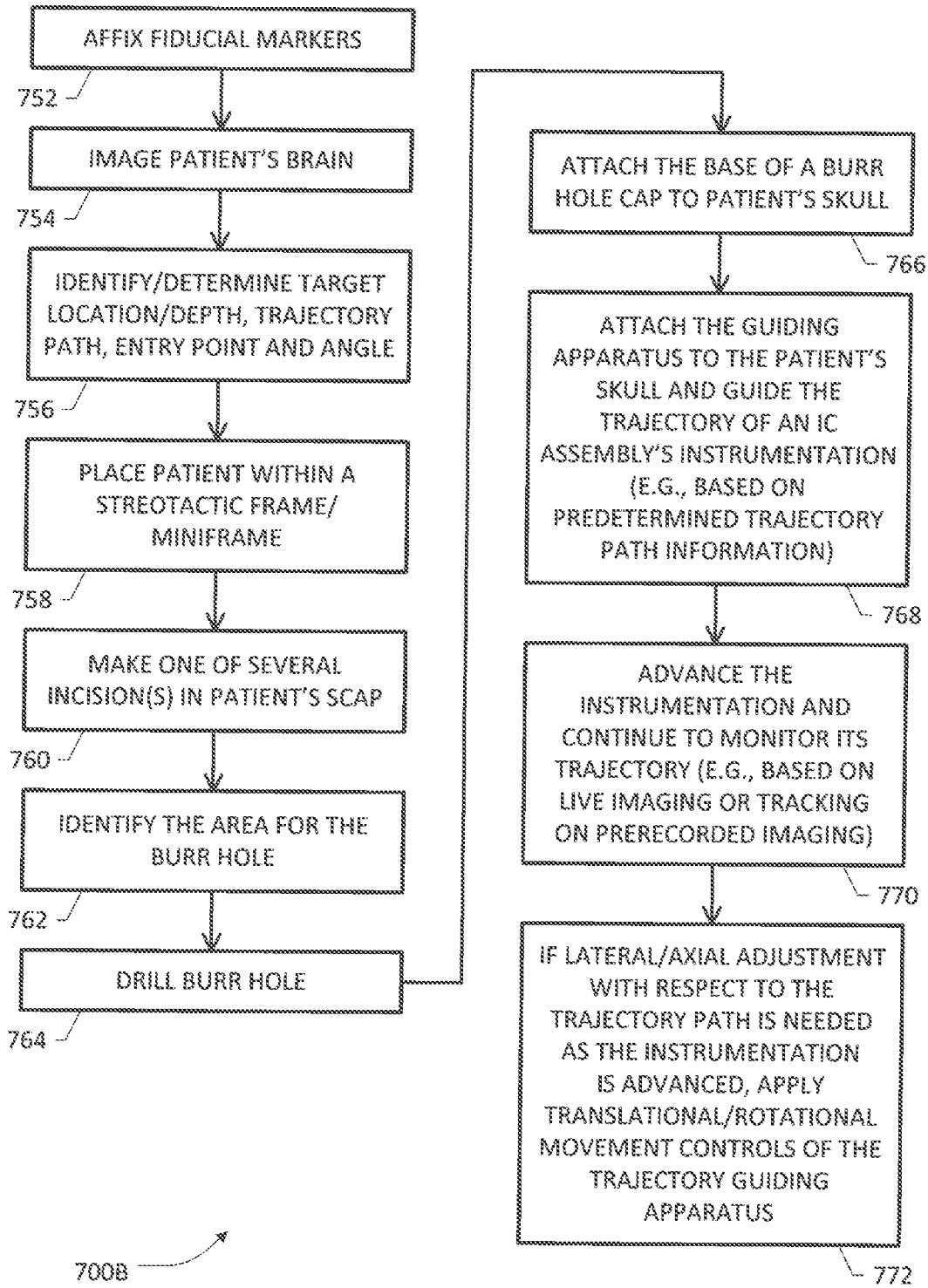

Turning to FIGS. 7A and 7B, depicted therein are flowcharts of various steps, blocks, acts and/or functions that may be combined in one or more (re)arrangements for purposes of practicing an example method according to one or more embodiments of the present disclosure. Process 700A is representative of a methodology or procedure for implanting an elongate medical device into a patient's brain using a trajectory guide apparatus of the present patent disclosure. At block 702, trajectory path information may be determined or otherwise obtained regarding at least one of a path entry point, a target location, a trajectory path and an entry angle with respect to implanting the elongate medical device through the patient's cranium, wherein the elongate medical device is configured to provide a particular therapy. For example, such information may be obtained at least in part based on suitable 2D, 3D or 4D imaging or scanning technologies in reference to the tissue region and the therapy plan being contemplated, e.g., computed tomography (CT) such as 2D/3D X-ray imaging/scanning based on computerized axial tomography (CAT scan), isocentric fluoroscopy, bi-plane fluroscopy, MRI as well associated 4D imaging (e.g., using movement or flow as the fourth dimension), optical coherence tomography (OCT), planar gamma scintigraphy (PGS), functional imaging techniques such as positron emission tomography (PET), single-photon emission computerized tomography (SPECTscan), functional MRI, magnetic source imaging (MSI) or magnetoencephalography (MEG), or indirectly by using interactive anatomical atlas programs that map a brain atlas image onto the stereotactic image of the brain. Some embodiments may also involve other types of image acquisition technologies such as 3D-transcranial ultrasound (TCU), contrast enhanced TCU, and the like. Various intra-cranial regions or other tissues may be mapped including but not limited to thalamus/sub-thalamus, hippocampus, anterior nucleus, amygdalohippocampal complex, basal ganglia, globus pallidus, cortex or white matter tracts afferent to or efferent from the abovementioned brain tissue, inter alia.

At block 704, one or more burr holes may be drilled based on the trajectory path information around the respective predetermined path entry points in the cranium in accordance with applicable surgical procedures and protocols depending on how many implantations are contemplated. At block 706, a trajectory guiding apparatus is provided and attached surrounding the burr hole in a close proximity with minimum discomfort to the patient while ensuring firm and secure attachment to the patient's cranium. Skilled artisans will recognize that appropriate care and/or caution may need to be exercised while attaching the guiding apparatus to the cranium, e.g., to avoid drilling into the cranial bone sutures for securing or anchoring a fastener. As previously noted, the trajectory guiding apparatus may be provided with a base plate configured to be secured to the cranium and encircle the burr hole as closely as possible, optionally aided by a burr hole alignment tool operative to engage with a base plate frame aperture. In one embodiment, it is contemplated that a removable tower portion of the trajectory guide apparatus containing an IC assembly that holds the elongate medical device is securely attached to the base plate prior to mounting the trajectory guide apparatus to the patient's cranium. In another embodiment, the base plate may be attached to the patient's cranium first and the tower portion of the trajectory guide apparatus may be subsequently mounted thereto. At block 708, a bottom stage slider (BSS) table of the trajectory guiding apparatus may be actuated or otherwise manipulated to cause a translational movement adjustment so as to align the IC assembly to the path entry point in the burr hole. If the predetermined entry point has changed or shifted to a new entry point within the burr hole after the burr hole was created, the BSS table may be actuated accordingly to (re)position the IC assembly containing the elongate medical device. Likewise, a rotational movement adjustment may be caused by actuating or otherwise manipulating a top stage slider (TSS) table of the trajectory guiding apparatus to align an axial angle of the IC assembly with the entry angle of the predetermined trajectory, which may be (re)aligned as well if needed after creating the burr hole (block 710). Thereafter, the elongate medical device may be advanced using a drive assembly associated with the IC assembly until the target location within the patient's brain is reached (block 712). In one arrangement, an intraoperative guiding and navigation system may be used in aiding the surgeon or an automated entity to monitor and guide the advancement of the elongate medical device along the predetermined trajectory path or a recalibrated trajectory path (e.g., if or when a blood vessel or other structure not previously captured in an image scan or brain atlas is encountered). If a path deviation is determined, at least one of a translational adjustment and a rotational adjustment may be applied by actuating at least one of the BSS table and the TSS table to realign the elongate medical device with the (new) trajectory path. Upon reaching the target location within the patient's brain, appropriate therapy (e.g., DBS, laser/radiation treatment, biopsy, catheter placement, drug delivery, neurological ablation or lesioning, etc.) may be applied as set forth at block 714. One skilled in the art will recognize that a variety of bio-imaging/scanning systems (for example such as those referred to hereinabove) may be employed for purposes of intraoperative monitoring and navigation. In a further and/or alternative arrangement, a 3D-navigational system configured to pinpoint device location on pre-recorded X-ray images may also be used for such purposes, thereby advantageously reducing exposure to X-rays during procedures and implants while facilitating intraoperative guidance and device navigation.

Various additional/alternative steps, blocks, acts and/or functions that may be combined in one or more (re)arrangements within the foregoing scheme are set forth as a process 700B shown in FIG. 7B which includes an example burr hole creation procedure. At block 752, fiducial markers or reference points are affixed to the patient's skull. At block 754, imaging of the patient's brain is performed. As noted previously, any suitable imaging technology can be utilized such as MRI systems, CT systems, etc. The imaging may also involve functional analysis of the brain in response to specific stimuli. For example, a functional MRI process may be performed in which stimuli is provided to the patient and the MRI imaging is utilized to identify the specific structures in the brain that respond to the stimuli. At block 756, based upon the imaging information, a target location is identified. Commercially available navigational software can be used to relate the fiducial markers to desired target location. Specifically, the navigational software uses the identified target location with the imaging information of the patient's brain and the fiducial markers to calculate a location for the burr hole and a path for traversal of an implantable medical device to the target location. Preferably, the location of the burr hole and the path are selected to avoid damaging relevant structures of the brain, wherein the trajectory may or may not comprise or follow a single straight path.

At block 758, the patient is placed within a stereotactic frame in a headrest. At block 760, one or more incision(s) may be made on the patient's scalp. At block 762, an identification of the area for the burr hole is made on the patient's skull within the area exposed by the incision(s). At block 764, the burr hole is drilled through the skull. In one example arrangement, a burr hole cap base may be attached to the patient's skull using surgical screws (block 766), which may be used later in order to facilitate attachment of a burr hole cap that is configured to secure and subcutaneously route the implantable medical device for interfacing with external and/or implantable pulse generation (EPG/IPG) circuitry and telemetry apparatus. Additional details regarding an example burr hole cap deployment system for securing a DBS lead may be found in U.S. Pat. No. 7,949,410, entitled "BURR HOLE CAP AND METHODS OF USE", which is incorporated herein by reference. At block 768, a guiding apparatus of the present patent disclosure is attached to the patient's skull to guide the trajectory of an IC assembly's instrumentation (e.g., an elongate implantable medical device) through the brain (e.g., based on predetermined trajectory path information). At block 770, as the instrumentation is advanced, its trajectory may be monitored (e.g., based on tracking on prerecorded imaging or live imaging). If lateral/axial adjustment with respect to the trajectory path is needed as the instrumentation is advanced, appropriate translational/rotational movement controls of the trajectory guiding apparatus may be actuated as set forth at block 772.

Figure 8:
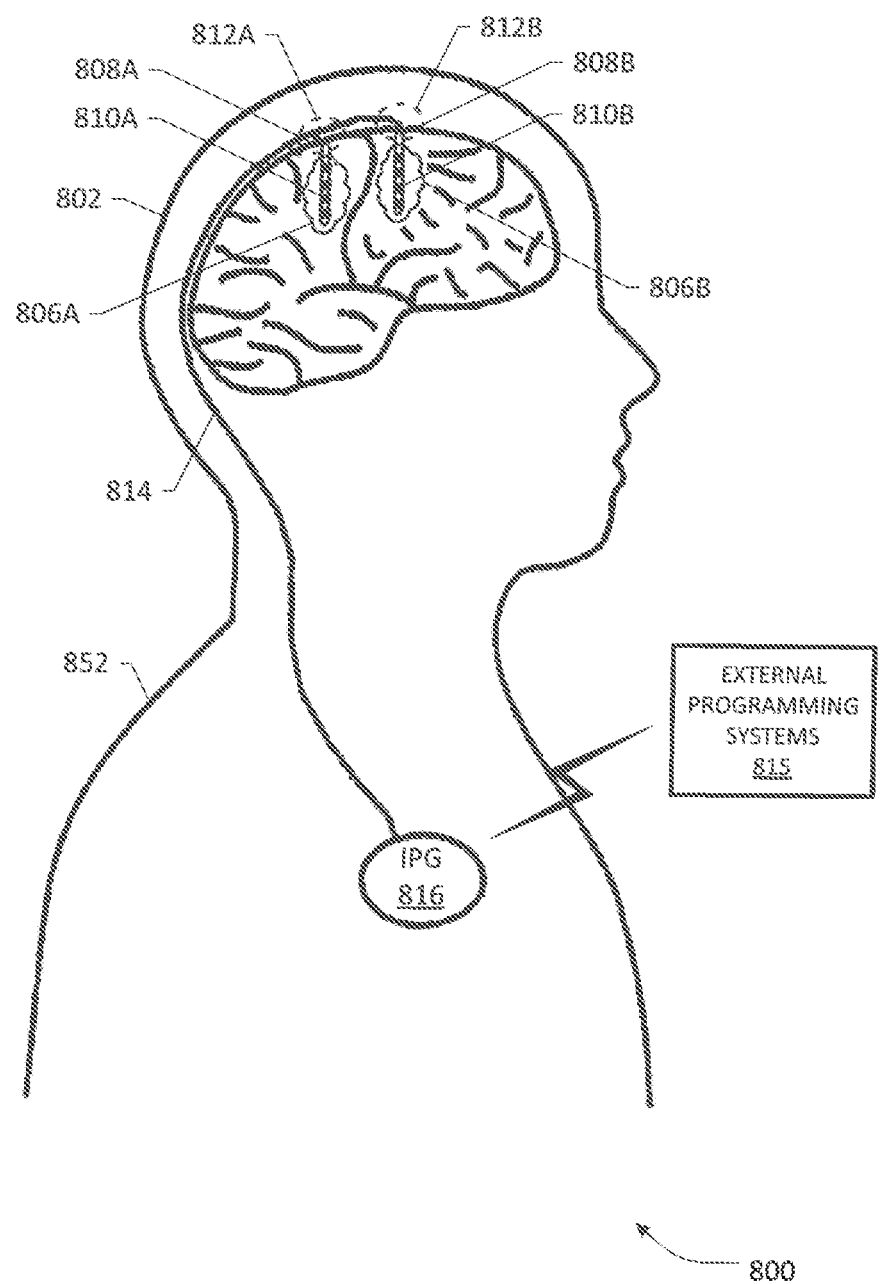
FIG. 8 is an illustrative diagram of a patient having one or more therapy leads implanted in different brain regions using a trajectory guide apparatus of the present disclosure according to the teachings herein.

FIG. 8 is an illustrative diagram of a therapy system 800 exemplifying a patient having one or more therapy leads implanted in different brain regions using a trajectory guide apparatus of the present disclosure according to the teachings herein. By way of illustration, a patient 852 is shown with two regions 806A and 800B of the patient's brain 804 that are implanted with respective DBS leads 808A and 808B, each guided and advanced by the trajectory guide apparatus of the present patent disclosure. Each DBS lead 808A/808B is exemplified as having a respective set of electrodes 810A, 810B. Further details regarding the leads 808A/808B as well as additional and/or alternative embodiments thereof may be found in the following: (i) U.S. Pat. No. 9,370,653, entitled "MEDICAL LEADS WITH SEGMENTED ELECTRODES AND METHODS OF FABRICATION THEREOF"; (ii) U.S. Pat. No. 8,463,387, entitled "STIMULATION OF THE AMYGDALOHIPPOCAMPAL COMPLEX TO TREAT NEUROLOGICAL CONDITIONS"; and (iii) U.S. Patent Application Publication No. 2018/0008821, entitled "IMPLANTABLE THIN FILM DEVICES", each of which is incorporated herein by reference. Respective burr holes 812A and 812B may be drilled in the patient's cranium 802 as described previously based on the desired therapy application, which may be spaced proximate to each other given that the base plate 102 and its frame portion 104 of the trajectory guide apparatus 100 is optimized to have a small form factor while providing requisite structural strength to the tower portion disposed above it. After completing the guided implantation of leads 808A/808B, the burr holes 812A and 812B may be capped and secured for routing the leads 808A/808B under the scalp of the patient 852. In one arrangement, electrical traces for the leads 808A/808B may be combined into a single lead body 814 that is routed subcutaneously to be coupled to an implanted pulse generator (IPG) 816, which may be electrically and/or telemetrically coupled to an external programming system 815 to provide appropriate therapy.

Based on the foregoing, skilled artisans will appreciate that embodiments herein provide a trajectory guiding apparatus that can advantageously benefit from a medical guided positioning system configured to provide lead placement trajectories with improved accuracy prior to actual lead implantation insertion without subsequent MRI scanning. Elimination of MRI scans during lead placement eliminates the need for an MRI Operating Room (OR) suite, thereby reducing implantation time and cost, while improving lead placement accuracy (e.g., in the sub-millimeter range in one implementation). When used in conjunction with such a guided positioning/navigation system that provides precise location information of the implantable instrumentation, e.g., the cannula, an embodiment of the present patent disclosure may be configured such that it allows the patients to remain under anesthesia (whereby the patients will not have to endure the pain of securing a tool to their skull). Further, embodiments herein are advantageously configured to minimize the screw size and number of screws used to secure the trajectory guide apparatus, thereby reducing potential discomfort to the patient. In a further variation, the base plate of the trajectory guide apparatus may be conformed to the contours of an individual patient's cranium such that a most comfortable fit or attachment may be obtained. Since the base plate is removable from the tower portion, different base plates may be provided for different patients, e.g., as a one-time use option, while the rest of the trajectory guide apparatus may be reused in multiple therapy applications.

In a still further variation, an embodiment of the trajectory guide apparatus may be provided with appropriate mechanical means to insert the instrumentation lead into the patient's brain by use of a direct drive mechanism (e.g., a mechanism that takes the power coming from a motor without any reductions such as a gearbox) for initial insertion and a reduction drive mechanism for precise final implantation positioning. It will be further appreciated that because a separate base is provided, an embodiment of the trajectory guide apparatus advantageously allows the surgeon to have full access to the burr hole and a tool to ensure alignment between the base and the burr hole.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

Although various embodiments have been shown and described in detail, the claims are not limited to any particular embodiment or example. It will be understood that numerous alterations, variations, modifications, and the like, of the embodiments may be practiced in accordance with the teachings herein. None of the above Detailed Description should be read as implying that any particular component, element, step, act, or function is essential such that it must be included in the scope of the claims. Reference to an element in the singular is not intended to mean "one and only one" unless explicitly so stated, but rather "one or more." Further, "a," "an," "the," "at least one," and "one or more" are used interchangeably herein at least with respect to certain embodiments. Moreover, the terms "first," "second," and "third," etc. employed in reference to elements or features are used merely as labels, and are not intended to impose numerical requirements, sequential ordering or relative degree of significance or importance on their objects. It is noted that the term "comprises" and variations thereof do not have a limiting meaning where these terms appear in the accompanying description and claims. Additionally, relative terms such as "left," "right," "front," "fore," "forward," "rear," "aft," "rearward," "top," "bottom," "side," "upper," "lower," "above," "below," "horizontal," "vertical," and the like may be used herein and, if so, are from the applicable perspective that may be observed with respect to the particular drawing. These terms are used only to simplify the description, however, and not to limit the interpretation of any embodiment described. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A trajectory guiding apparatus, comprising:
a base plate comprising a frame portion with a plurality of laterally extending support members, the frame portion having a first aperture sized to surround a burr hole opening in a patient's cranium, the frame portion configured for fastening the base plate to the cranium;
a base frame comprising:
a plurality of legs corresponding to the plurality of laterally extending support members of the base plate, each leg having a top terminus and a bottom terminus, wherein the plurality of legs are securely coupled at respective bottom termini to the corresponding laterally extending support members; and
a first platform securely coupled to the plurality of legs at respective top termini, the first platform having a second aperture with at least a same size as the first aperture of the frame portion; and
a dual-stage slider (DSS) assembly comprising a bottom stage slider (BSS) table and a top stage slider (TSS) table, the BSS table slidably engaged to the first platform and the TSS table coupled to the BSS table via a second platform disposed between the BSS table and the TSS table, the second platform having a third aperture, wherein the BSS table is provided with a bottom spherical bearing having a first diameter and the TSS table is provided with a top spherical bearing having a second diameter larger than the first diameter, the bottom and top spherical bearings each having a respective axial bore therethrough, the respective axial bores axially aligned and sized to accommodate an instrumentation column having a columnar passage therethrough and coupled to a drive assembly for advancing a distal end of an elongate medical device through the columnar passage of the instrumentation column, wherein the BSS and TSS tables are independently actuatable and further wherein the BSS table is actuatable to move the instrumentation column on a translational motion plane substantially parallel relative to a burr hole plane that is co-planar with the burr hole and the TSS table is actuatable to pivotally rotate the instrumentation column, with the bottom spherical bearing operating as a fulcrum, to change a trajectory angle of the instrumentation column relative to a perpendicular axis orthogonal to the burr hole plane.

2. The trajectory guiding apparatus as recited in claim 1, wherein the BSS table further comprises:
a bottom lower plate slidably engaged with a grooved surface of the first platform; and
a bottom upper plate slidably engaged with the bottom lower plate and rigidly coupled to the second platform, wherein the bottom lower plate is operative to slide along a first axis and the bottom upper plate is operative to slide along a second axis, the first and second axes orthogonal to each other and disposed along the translational motion plane, and
wherein a first slider table aperture is defined through the bottom lower plate and the bottom upper plate, the first slider table aperture extending into a funnel coupled to the bottom lower plate, the funnel tapering from a wider orifice at the bottom lower plate to a narrower orifice proximate to the burr hole, the narrower orifice of the funnel sized to contain a first ring liner operative to secure the bottom spherical bearing for allowing rotational movement.

3. The trajectory guiding apparatus as recited in claim 2, wherein the TSS table further comprises:
a top lower plate slidably engaged with a grooved surface of the second platform; and
a top upper plate slidably engaged with the top lower plate, wherein the top lower plate is operative to slide along the first axis and the top upper plate is operative to slide along the second axis,
wherein a second slider table aperture is defined through the top lower plate and the top upper plate, the second slider table aperture having an angled surface tapering from a wider orifice at the top upper plate to a narrower orifice at the top lower plate, the narrower orifice of the top lower plate sized to contain a second ring liner operative to secure the top spherical bearing for converting a translational movement of at least one of the top lower plate and the top upper plate into a rotational movement of the instrumentation column around the perpendicular axis.

4. The trajectory guiding apparatus as recited in claim 3, wherein the frame portion of the base plate comprises an annular structure having a circular orifice forming the first aperture, the circular orifice sized to surround the burr hole in a close proximity.

5. The trajectory guiding apparatus as recited in claim 4, wherein the axial bore of the bottom spherical bearing is narrower than the axial bore of the top spherical bearing, and wherein a distal end of the instrumentation column is thinned to be accommodated as a pivot in the axial bore of the bottom spherical bearing.

6. The trajectory guiding apparatus as recited in claim 5, wherein the frame portion includes a minimum number of holes for securely fastening the base plate to the cranium with screws of biocompatible and magnetic resonance imaging (MRI) compatible material.

7. The trajectory guiding apparatus as recited in claim 6, wherein the plurality of legs of the base frame comprise three legs spaced apart to allow a maximum access to the burr hole during a neurological procedure performed on the patient.

8. The trajectory guiding apparatus as recited in claim 7, wherein a maximum angular displacement of the rotational movement effectuated by the TSS table is determined by at least one of (i) an angle of the angled surface of the second slider table aperture; (ii) a ratio of a diameter of the wider orifice of the second slider table aperture to a diameter of the narrower orifice of the second slider table aperture; and (iii) a combined thickness of the top upper plate and the top lower plate.

9. The trajectory guiding apparatus as recited in claim 7, wherein at least one of the plurality of legs is coupled to a corresponding laterally extending support member of the base plate with a screw and each remaining leg is attached to a corresponding laterally extending support member of the base plate in a sliding snap fit arrangement to facilitate ease of disassembly.

10. The trajectory guiding apparatus as recited in claim 7, wherein the instrumentation column includes a vertical opening to the columnar passage to allow a tension member of the drive assembly to frictionally hold the elongate medical device within the columnar passage.

11. The trajectory guiding apparatus as recited in claim 10, wherein the drive assembly is at least one of a manually operable drive assembly and a motorized drive assembly.

12. The trajectory guiding apparatus as recited in claim 7, wherein each of the bottom lower plate, the bottom upper plate, the top lower plate and the top upper plate is actuated by a screw drive.

13. The trajectory guiding apparatus as recited in claim 12, wherein each screw drive is operative by at least one of a manually operable drive assembly and a motorized drive assembly.

14. The trajectory guiding apparatus as recited in claim 13, wherein each of the bottom lower plate, the bottom upper plate, the top lower plate and the top upper plate is provided with a corresponding measurement gauge for indicating a measurement of at least one of a translational movement and a rotational movement.

15. The trajectory guiding apparatus as recited in claim 7, wherein the base plate, the base frame, the dual-stage slider assembly and the instrumentation column are formed of biocompatible and magnetic resonance imaging (MRI) compatible materials.

16. The trajectory guiding apparatus as recited in claim 7, wherein the elongate medical device comprises at least one of a deep brain stimulation (DBS) lead comprising a plurality of electrodes at a distal end, a biopsy instrumentation device, a catheter insertion device, an injection and aspiration device, a neurological endoscopy device, a microelectrode recording (MER) device, a macro stimulation device, a cannula device, a neurological ablation device, and a brain lesioning device.

* * * * *

UNITED STATES PATENT AND TRADEMARK OFFICE
CERTIFICATE OF CORRECTION

PATENT NO. : 11,406,470 B2
APPLICATION NO. : 16/265674
DATED : August 9, 2022
INVENTOR(S) : Robert E. Jones et al.

It is certified that error appears in the above-identified patent and that said Letters Patent is hereby corrected as shown below:

In the Specification

At Column 8, Line number 46, delete "plate 1448" and replace with --plate 144B--.

Signed and Sealed this
Fourth Day of October, 2022

*Katherine Kelly Vidal*

Katherine Kelly Vidal
*Director of the United States Patent and Trademark Office*